US008735177B2

(12) United States Patent
Sakuma et al.

(10) Patent No.: US 8,735,177 B2
(45) Date of Patent: May 27, 2014

(54) DIAGNOSTIC MARKER

(75) Inventors: Shinji Sakuma, Osaka (JP); Shinji Yamashita, Osaka (JP); Ken-Ichiro Hiwatari, Tokyo (JP); Yoshikazu Shoji, Tokyo (JP)

(73) Assignee: Adeka Corporation, Tokyo (JP)

( * ) Notice: Subject to any disclaimer, the term of this patent is extended or adjusted under 35 U.S.C. 154(b) by 902 days.

(21) Appl. No.: 11/918,465

(22) PCT Filed: Feb. 20, 2007

(86) PCT No.: PCT/JP2007/053068
§ 371 (c)(1), (2), (4) Date: Oct. 15, 2007

(87) PCT Pub. No.: WO2007/097318
PCT Pub. Date: Aug. 30, 2007

(65) Prior Publication Data
US 2009/0075301 A1    Mar. 19, 2009

(30) Foreign Application Priority Data

Feb. 23, 2006  (JP) ................................. 2006-046412

(51) Int. Cl.
*G01N 33/547* (2006.01)
*G01N 33/544* (2006.01)

(52) U.S. Cl.
USPC ......................................... 436/532; 436/528

(58) Field of Classification Search
None
See application file for complete search history.

(56) References Cited

U.S. PATENT DOCUMENTS

| | | | |
|---|---|---|---|
| 5,968,479 A | 10/1999 | Ito et al. | |
| 6,066,310 A | 5/2000 | Konishi et al. | |
| 6,083,485 A * | 7/2000 | Licha et al. | ..................... 424/9.6 |
| 6,084,072 A * | 7/2000 | Rinderle et al. | ............... 530/370 |
| 6,258,340 B1 | 7/2001 | Licha et al. | |
| 6,331,289 B1 | 12/2001 | Klaveness et al. | |
| 6,913,743 B2 | 7/2005 | Licha et al. | |
| 6,926,885 B2 | 8/2005 | Licha et al. | |
| 7,025,949 B2 | 4/2006 | Licha et al. | |
| 7,445,767 B2 | 11/2008 | Licha et al. | |
| 7,655,217 B2 | 2/2010 | Licha et al. | |
| 2005/0106106 A1 | 5/2005 | Licha et al. | |
| 2005/0169844 A1 | 8/2005 | Licha et al. | |
| 2006/0281076 A1 * | 12/2006 | Marla et al. | ........................ 435/5 |

FOREIGN PATENT DOCUMENTS

| | | |
|---|---|---|
| EP | 1 181 940 | 2/2002 |
| JP | 10-510250 A | 10/1998 |
| JP | 10-307138 A | 11/1998 |
| JP | 2002-348564 A | 12/2002 |
| JP | 2005-505580 A | 2/2005 |
| JP | 3669752 B2 | 4/2005 |
| WO | 91/06865 | 5/1991 |
| WO | 02/067850 | 9/2002 |
| WO | 03/028527 | 4/2003 |
| WO | 2004/081027 | 9/2004 |

OTHER PUBLICATIONS

Journal of Pharmaceutical Science and Technology, Japan, 2005, vol. 65, No. 5, pp. 284-288.
Notice of Rejection mailed Jun. 12, 2012 by the Japanese Patent Office in Japanese Patent Application No. 2007-515723 with English translation, 10 pages.
European Search Report—PCT/JP2007/053068—Oct. 24, 2012.

* cited by examiner

*Primary Examiner* — Shafiqul Haq
(74) *Attorney, Agent, or Firm* — Young & Thompson

(57) ABSTRACT

A diagnostic marker is composed of particles that have a diameter of from 1 nm to 100 µm, the particles possessing on their surfaces a site that has a high specific bonding ability to a specific antigen residing on the mucosa of digestive cancers and a site that has a low bonding ability to the mucosa of digestive organs, and further incorporating an identification material.

6 Claims, No Drawings

DIAGNOSTIC MARKER

TECHNICAL FIELD

The present invention relates to a diagnostic marker for early detection and treatment of digestive cancers with an endoscope.

BACKGROUND ART

Malignant tumors developed in the food passing, digesting, and absorbing organs such as the esophagus, stomach, duodenum, small intestine, and large intestine are classified into digestive cancers that are one of serious disorder groups, having a large number of patients along with lung cancer and breast cancer. Among them, large intestine cancer is ranked high in the number of occurrences and fatalities, regardless of the region of Japan, United States, or Europe, or the patient sex of male or female (the annual number of patients in each region: 100,000 or more). Stomach cancer has such a specificity that the occurrence frequency is high in Japan (the annual number of patients: about 100,000), but an annual number of patients as large as 10,000 is reported in United States or European countries. Esophagus cancer has a smaller number of incidence as compared with large intestine cancer and stomach cancer, but is ranked at 6th of the list for male Japanese (the occurrence ratio of male:female is 6:1), and over 10,000 of people suffer every year. Although the number of patients and fatalities of digestive cancer is large, but if the cancer is in an early stage in which the cancer remains in polyp and mucosa, the cancer can be cured by endoscopic mucosal resection.

However, when the lesion outstretches the large intestine wall, the intestine is surgically removed. Further, if the detection of the cancer is delayed and there is a distant metastasis, the cancer is treated by combining chemotherapy with surgical therapy. As a chemotherapy drug against large intestine cancer, promising new drugs such as Oxaliplatin, a platinum-based drug and Avastin, an antibody drug have been developed in recent years. However, these drugs do not provide a sufficient therapeutic outcome.

The best therapy for these digestive cancers is early detection and focal site resection. Cancer develops from the mucosal side. In the case of early cancer where the focal site remains in the mucosa, endoscopic mucosal resection is an adequate treatment. If the application of this treatment expands, a number of plus factors including reduction of patient burden, improvement of therapeutic outcome, and improvement of medical economics would be expected.

However, the present diagnosis with an endoscope still stays at the stage where only a tumor as large as 1 to 2 cm can be detected, with which a risk of metastasis to multiple organs increases abruptly.

In view of the circumstances as described above, a diagnostic marker that can stain specifically cancer cells or tissues has been attempted, and is disclosed, for example, in Patent Document 1.

However, this diagnostic marker is composed of a fluorescence compound bound to an antibody that specifically binds to cancer cells or tissues (or is composed of a fluorescent functional group incorporated into the antibody). The diagnostic marker certainly can stain cancer tissues or their peripheral mucosal tissues. But the diagnostic marker binds to normal tissues to some extent besides the cancer tissues, and also the amount of the fluorescence compound per antibody is small, so that the contrast between the cancer tissues and normal tissues is low, and that the marker does not provide a high diagnostic accuracy.

Patent Document 1: Japanese Patent No. 3669752

DISCLOSURE OF THE INVENTION

Problems to be Solved by the Invention

Therefore, it is an object of the present invention to provide a diagnostic marker that has a capability of enhancing the contrast between the cancer tissues and normal tissues and is advantageous for early detection and treatment of digestive cancers using an endoscope, and to provide a method for producing the diagnostic marker.

Means for Solving the Problems

In order to accomplish the above-mentioned objectives, the present invention provides a diagnostic marker that is composed of particles having a diameter of from 1 nm to 100 μm, the particles possessing on their surfaces a site having a high specific bonding ability to a specific antigen residing on the mucosa of digestive cancers and another site having a low bonding ability to the mucosa of digestive organs, and having an identification material incorporated therein.

The present invention also provides a method for producing the diagnostic marker. The method is characterized in that a macro-monomer represented by the formula (4) and/or another macro-monomer represented by the formula (5), still another macro-monomer represented by the formula (6), and styrene are polymerized in a polar solvent to obtain polymer fine particles; a fluorescence luminescent material is incorporated in the resulting polymer fine particles, or a fluorescence luminescent material is incorporated in the polymer fine particles at the same time with the formation of the polymer fine particles by allowing the fluorescence luminescent material present in the polymerization system when the macro-monomer represented by the formula (4) and/or the macro-monomer represented by the formula (5), the macro-monomer represented by the formula (6), and styrene are polymerized in the polar solvent, and then, an antibody and/or lectin are(is) bonded or adsorbed on the surfaces of the polymer fine particles.

[Formula 1]

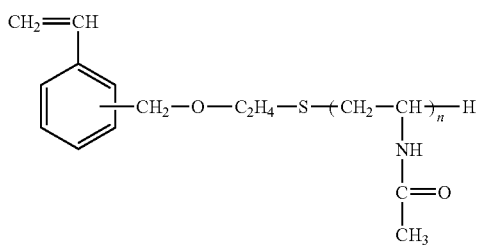

(4)

(In the formula, n is the same as in formula (3).)

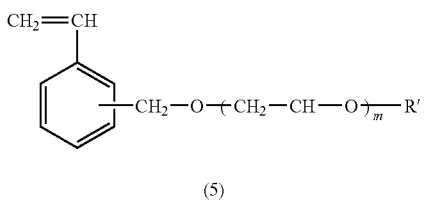

[Formula 2]

(5)

(In the formula, R' and m are the same as in formula (3).)

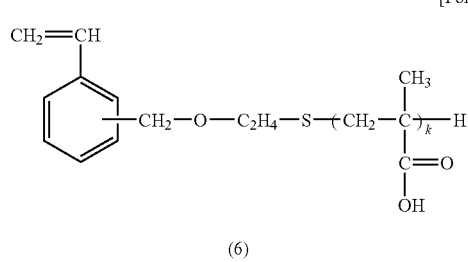

[Formula 3]

(6)

(In the formula, k is the same as in formula (3).)

BEST MODE FOR CARRYING OUT THE INVENTION

Firstly, the diagnostic marker of the present invention is explained with a preferred exemplary embodiment.

There is not any particular limitation on the particles used in the present invention as long as the particles have a diameter of from 1 nm to 100 μm, possess on their surfaces a site having a high specific bonding ability to a specific antigen residing on the mucosa of digestive cancers and another site having a low bonding ability to the mucosa of digestive organs, and incorporate an identification material therein. Any base material may be used for the particles without limitation, that includes inorganic particles such as silica and organic polymers such as polystyrene and poly(meth)acrylate, but the organic polymers are preferably selected in view of dispersing stability in water or physiological saline solution.

The above particles are required to have a diameter of from 1 nm to 100 μm, preferably from 10 nm to 100 μm, more preferably from 50 nm to 100 μm, and most preferably from 100 nm to 10 μm. Too small and too large particle diameter cannot provide a high contrast between the cancer tissues and normal tissues.

The particles contained in the diagnostic marker of the present invention possess on their surfaces a site having a high specific bonding ability to a specific antigen residing on the mucosa of digestive cancers.

There is not any particular limitation on the site having a high specific bonding ability to a specific antigen residing on the mucosa of digestive cancers, but there may be mentioned, preferably an antibody and/or lectin, and more preferably lectin for example.

For example, in the case of large intestine cancer, it is known that the site of large intestine cancer exhibits a different sugar-chain structure from the surface of normal mucosa owing to the malignant alteration of the large intestine mucosa cells. Among the sugar-chain structure, galactosyl β1-3-N-acetylgalactosamine residue (hereinafter in some cases, referred to as TF antigen) is well known.

Lectin is known to have a high specific bonding ability to the TF antigen. There may be exemplified *Arachis hypogaea* (peanuts lectin, hereinafter in some cases, abbreviated as PNA), *Agavicus bisporus* (mashroom lectin, hereinafter in some cases, abbreviated as ABA), *Bauhinia purpurea* (hereinafter in some cases, abbreviated as BPA), and others. The particles having on their surfaces these materials may acquire a site having a high specific bonding ability to a specific antigen residing on the mucosa of digestive cancers.

These lectins may be used as a diagnostic marker for digestive cancers in general since the TF antigen is expressed also in digestive cancers other than large intestine cancer. In particular, expression of the TF antigen is remarkable especially in large intestine cancer, so that these lectins are particularly preferably used as a diagnostic marker for large intestine cancer.

In addition, since there appear N-acetylneuraminic acid, α2,6-bonded N-acetylgalactosamine (sialylTn) or the like in digestive cancers owing to the malignant alteration of the cells, a lectin having a high specific bonding ability to these antigens can be also selected.

Furthermore, as an identification molecule for digestive cancer cells, other than lectins, there can be selected, antibodies such as, for example, commercially available anti-Thomsen Friedenreich Antigen, mouse monoclonal, and clone A78-G/A7.

In order to attain a site having a high specific bonding ability to a specific antigen residing on the mucosa of digestive cancers, there is not any particular limitation on the method of incorporating into the surface of the particles a material that has a high specific bonding ability to the specific antigen residing on the mucosa of digestive cancers. A method that employs covalent bonding is most preferable, but physisorption may be employed.

There is not any limitation on the method of bonding through covalent boding the material having a high specific bonding ability to a specific antigen residing on the mucosa of digestive cancers, but most preferable is that the material is incorporated by forming an amide bonding with the help of a condensation agent (such as carbodiimide) that is used generally to fix proteins and peptides. There is not any particular limitation on the condensation agent that is used here, but particularly preferable are 1,3-dicyclohexyl carbodiimide (DCCD) and 1-ethyl-3-(3'-dimethylaminopropyl) carbodiimide (WSCI).

There is also not particular limitation on the site of the surface of the particles that has a low bonding ability to the mucosa of digestive organs and resides in the particles contained in the diagnostic marker of the present invention, but preferably is a site that is nonionic and has a high hydration force. For example, a polymer chain having N-vinylacetamide as a structural unit, a polyethylene glycol chain, or the like are preferable as the site having a low bonding ability to the mucosa of digestive organs.

Specifically, the site having a low bonding ability to the mucosa of digestive organs preferably contains the structure represented by formula (1) and/or the structure represented by formula (2) below.

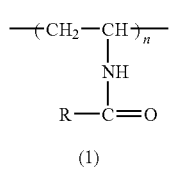

[Formula 4]

(1)

(In the formula, R is hydrogen atom or a hydrocarbon group having from 1 to 4 carbon atoms; and n is any number of from 10 to 400, preferably from 15 to 200, more preferably from 20 to 100, and still more preferably from 20 to 55.)

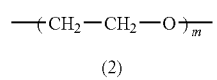

[Formula 5]

(2)

(In the formula, m is any number of from 10 to 400, preferably from 15 to 200, and more preferably from 20 to 100.)

As the particles that have on their surfaces the site having a high specific bonding ability to a specific antigen residing on the mucosa of digestive cancer and the site having a low bonding ability to the mucosa of digestive organs, there is exemplified preferably a particle that contains as a main ingredient a polymer having the structure represented by formula (3).

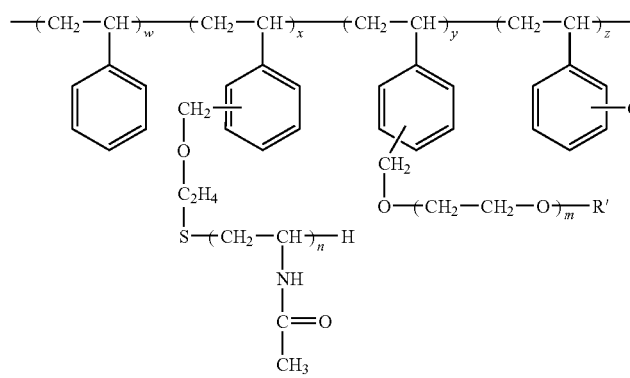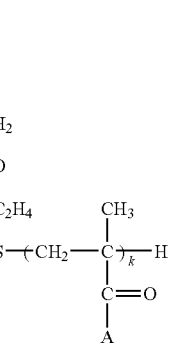

[Formula 6]

(3)

(In the formula, R' is hydrogen atom or a hydrocarbon group having from 1 to 4 carbon atoms; n is the same as in the above formula (1); m is the same as in the above formula (2); k is any number of from 10 to 200, preferably from 10 to 150, and more preferably from 20 to 100; A is lectin; w, x, y, and z, each is a number that allows the present polymer to have a molecular weight of from 10,000 to 1,000,000, and (x+y):z:w is from 1:0.2 to 2.5:5 to 300, preferably from 1:0.2 to 2.5:10 to 200, and more preferably from 1:0.2 to 2.5:20 to 100; either one of x and y may be 0; and the order of each repeating unit corresponding to each repeating unit number of w, x, y, and z is arbitrary in the main chain of the present polymer.)

Here, the polymer having the structure represented by the above formula (3) may have the other structure, for example, polymethacrylic acid, polymethylmethacrylate, polyvinylpyridine, polyvinylpyrolidone, polyvinylamine, polyacrylic acid, polyethylene glycol, polypropylene glycol, or the like, as long as the effect of the present invention is not impaired.

The particles used for the diagnostic marker of the present invention possess on their surfaces the site that has a high specific bonding ability to a specific antigen residing on the mucosa of digestive cancers and the site that has a low bonding ability to the mucosa of digestive organs, as described above.

The particles used for the diagnostic marker of the present invention may only reflect the characteristics of strong or weak bonding ability of two sites: a site that has a high specific bonding ability to a specific antigen residing on the mucosa of digestive cancer; and a site that has a low bonding ability to the mucosa of digestive organs. These sites do not necessary reside on the very fringe of the outmost layer of the particles, but may reside inside of the particles up to about 10 nm deep from the fringe of the outmost layer, which defines "the surface of the particles" on which these sites are present according to the invention. Therefore, in the case of the particles that have a diameter of 20 nm or less, "the surface of the particles" is the same meaning as merely saying "in the particles". The sites may reside in such a manner as well.

The amount of the molecular structure that resides inside of the particles up to 10 nm deep from the fringe of the outmost layer can be estimated by X-ray photoelectron spectroscopy (XPS). When lectins and others are bonded after the particles are formed, the lectins and others naturally reside on the surfaces of the particles. In this case, the amount of the molecular structure can be obtained by estimating the amount of the lectins and others contained in the whole particle.

There is not any particular limitation on the identification material incorporated in the particles used for the diagnostic marker of the present invention, as long as the identification material can be detected by any method of the endoscope observation, the naked eye observation, and the observation using an instrument such as a spectrometer and a fluorescence photometer. The identification material is preferably a fluorescence luminescent material.

The fluorescence luminescent material may include, for example, fluoresceins, rhodamines, coumarins, dansyls, NBD-type dyes, phycobiliproteins, and BODIPY derivatives. Further, a derivative that is given by combining these fluorescence luminescent materials with a highly hydrophobic material (for example, cholesterol or the like) can be used.

Among these, considering sensitivity and light sources used, most preferable are the fluorescence luminescent material such as fluoresceins and their derivatives (for example, labeled cholesterol that is given by combining cholesterol and fluoresceins), and coumarins that have a high luminescence intensity and is water-soluble (for example, coumarin6 or the like).

There is also not any particular limitation on the method of incorporating the fluorescence luminescent material into the above-mentioned particles, as long as sensitivity required for identification is maintained and no flowing out to water environment occurs. For example, in the course of the particle synthesis, the fluorescence luminescent material may be incorporated into the synthesis reaction system so as to be sandwiched between the molecules of the particles. As a preferred specific example of the foregoing fluorescent luminescent material, there may be mentioned coumarin6 (Coumarin 6, manufactured by Sigma-Aldrich Corp.).

Furthermore, after the particles are synthesized, the fluorescent luminescent material may be incorporated by absorbing it in the particles. As a preferred specific example of the foregoing fluorescent luminescent material, there may be mentioned a labeled cholesterol (also called as fluoresceinated cholesterol) that is given by combining fluorescein-5-carbonyl azide, diacetate (F6218, manufactured by Molecular Probes Corp.) with a highly hydrophobic cholesterol. Such labeled cholesterol is preferred, because the fluorescence luminescent material can be easily incorporated into the polymer particles by absorbing the fluorescence luminescent material into the inside of the particles after the particles are synthesized.

The residing amounts (concentration) of the site that has a high specific bonding ability to a specific antigen residing on the mucosa of digestive cancers, the site that has a low boding ability to the mucosa of digestive organs, and the identification material are as follows.

The residing amount (concentration) of the site that has a high specific bonding ability to a specific antigen residing on the mucosa of digestive cancers: the residing amount per 1 g of the particles is preferably from 1 mg/g to 1 g/g, more preferably from 1 mg/g to 100 mg/g, and still more preferably from 2 mg/g to 50 mg/g.

The residing amount (concentration) of the site that has a low boding ability to the mucosa of digestive organs: preferably from 1 to 99% by mass, more preferably from 5 to 90% by mass, and still more preferably from 20 to 70% by mass.

The residing amount (concentration) of the identification material: preferably from 0.005 to 5% by mass, and more preferably from 0.01 to 1% by mass.

The diagnostic marker of the present invention contains the particles as described above. The particles may be contained in any mode, but preferably in a mode in which the particles are dispersed in a dispersion medium. In this case, there is not any particular limitation on the dispersion medium, as long as the medium is less toxic to living organisms and does not inactivate the protein contained in the above particles. For example, an aqueous dispersion medium that is known to be used for pharmaceutical or medical preparation can be used. As an example of the dispersion medium, there may be mentioned physiological saline solution, phosphate buffered saline solution (the solution may contain or may not contain Ca or Mg), and others.

The concentration of the above-mentioned particles contained in the diagnostic marker of the present invention is not particularly limited, but is preferably from 0.01 µg/mL to 990 mg/mL, more preferably from 0.1 µg/mL to 10 mg/mL, and still more preferably from 0.5 µg/mL to 1 mg/mL, since the diagnosis efficiency decreases at extremely low concentrations, and the fluidity decreases and also the diagnosis efficiency decreases at extremely high concentrations.

The diagnosis marker of the present invention may optionally contain an additive, that is known to be used in the pharmaceutical or medicinal preparation, in an amount that the additive is conventionally used, as long as the effect of the present invention is not impaired.

Next, a preferred method for producing the diagnostic marker of the present invention will be explained.

The diagnostic marker of the present invention is prepared as follows: a macro-monomer represented by the formula (4) and/or another macro-monomer represented by the formula (5), still another macro-monomer represented by the formula (6), and styrene are polymerized in a polar solvent to obtain polymer fine particles; a fluorescence luminescent material is incorporated in the resulting polymer fine particles, or a fluorescence luminescent material is incorporated in the polymer fine particles at the same time with the formation of the polymer fine particles by allowing the fluorescence luminescent material present in the polymerization system when the macro-monomer represented by the formula (4) and/or the macro-monomer represented by the formula (5), the macromonomer represented by the formula (6), and styrene are polymerized in the polar solvent; and then, an antibody and/or lectin is bonded or adsorbed on the surfaces of the polymer fine particles.

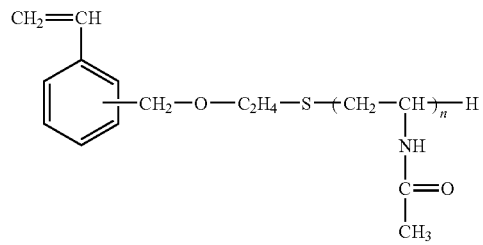

[Formula 7]

(4)

(In the formula, n is the same as in the above formula (3).)

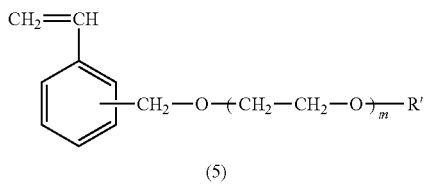

[Formula 8]

(5)

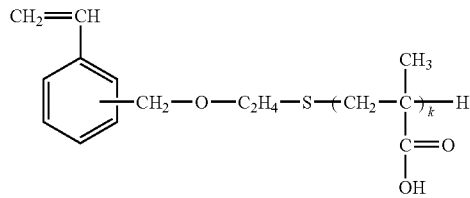

[Formula 9]

(6)

(In the formula, k is the same as in the above formula (3).)

Any method may be employed for preparing the macromonomer represented by the above formula (4), and the method is not particularly limited. The macro-monomer may be prepared in accordance with conventional methods, but, for example, may be prepared as follows: firstly, a polymer represented by the following formula is obtained, for example, by using 2-mercaptoethanol as a starting material, and polymerizing N-vinylacetamide (NVA) in an organic solvent (for example, toluene or the like) in the presence of a polymerization initiator (for example, N,N-azobisisobutyronitrile (AIBN) or the like);

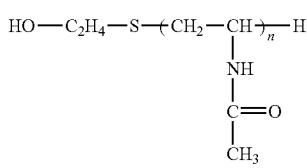
[Formula 10]

(In the formula, n is the same as in the above formula (4).)

And then, the resulting polymer is reacted with vinylbenzylchloride (for example, the reaction is carried out in a solvent of dimethylformamide and in the presence of NaH and tetrabutylphosphonium bromide) so as to obtain the objective macro-monomer.

Any method may be employed for preparing the macro-monomer represented by the above formula (5), and the method is not particularly limited. The macro-monomer may be prepared in accordance with conventional methods, but, for example, may be prepared as follows: polyethylene glycol is prepared through conventional polymerization; and then, the polyethylene glycol (or its derivative with alkylated end group obtained by further reacting the polyethylene glycol with sodium hydroxide and the like, and then with an alkylchloride such as methylchloride) is reacted with vinylbenzylchloride.

Any method may be employed for preparing the macro-monomer represented by the above formula (6), and the method is not particularly limited. The macro-monomer may be prepared in accordance with conventional methods, but, for example, may be prepared as follows: firstly, a polymer represented by the following formula is obtained, for example, by using 2-mercaptoethanol as a starting material, and polymerizing tert-butylmethacrylate (t-BMA) in an organic solvent (for example, THF or the like) in the presence of a polymerization initiator (for example, N,N-azobisisobutyronitrile (AIBN) or the like);

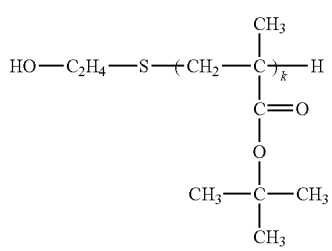
[Formula 11]

(In the formula, k is the same as in the formula (6).)

Then, the resulting polymer is reacted with vinylbenzylchloride (for example, the reaction is carried out in a solvent of dimethylformamide and in the presence of NaH and tetrabutylphosphonium bromide); and then the t-Bu group is eliminated by hydrolysis so as to obtain the objective macro-monomer.

In the method for producing the diagnostic marker of the present invention, firstly, the macro-monomer represented by the above formula (4) and/or the macro-monomer represented by the above formula (5), the macro-monomer represented by the above formula (6), and styrene are polymerized in a polar solvent to obtain polymer fine particles.

The ratio of these macro-monomers and styrene is represented as ([4]+[5])[6][S]=1:0.2 to 2.5:5 to 300, wherein [4] is the number of moles for the macro-monomer represented by the above formula (4); [5] is the number of moles for the macro-monomer represented by the above formula (5); [6] is the number of moles for the macro-monomer represented by the above formula (6); and [S] is the number of moles for styrene. The above ratio is based on the number of moles for each macro-monomer or monomer that is actually involved in the polymerization. When the reaction rate of each macro-monomer or monomer does not reach 100% owing to the reaction conditions and others, the ratio of macro-monomer or monomer actually used in the polymerization may be allowed not to be within the above ratio.

There is not any particular limitation on the above polar solvent, but there may be used a known polar solvent including, for example, an inorganic polar solvent such as water, an organic polar solvent such as ethanol, and a mixed solvent of these inorganic and organic polar solvents. Considering the solubility or dispersibility of the macro-monomers or monomer, preferably used are an organic polar solvent such as ethanol or a mixed solvent of the organic polar solvent and an inorganic polar solvent such as water (the amount of the inorganic polar solvent is preferably 30% by volume or less in the mixed solvent).

The polymerization of these macro-monomers and monomer can be performed with a known reaction condition, for example, by using a catalyst such as AIBN and reacting at 40° C. to 80° C. for 3 hours to 48 hours.

The polymer obtained by polymerizing these macro-monomers and monomer in the above polar solvent is aggregated into particles. The outside of the particles is composed of the structural unit that is derived from the macro-monomers represented by the above formulas (4) to (6) and has a high solubility to the polar solvent. The inside of the particles is composed of the structural unit that is derived from styrene and has a low solubility to the above polar solvent. As a result, the polymer fine particles thus obtained have on their surfaces the structure represented by the above formulas (1) and/or the structure represented by the above formula (2). In addition, similarly, the particles possess on their surfaces the structural units derived from the macro-monomers represented by the above formulas (4) to (6).

Polymer fine particles thus obtained have a diameter of around 50 nm to 100 μm when the molecular weight of the resulting polymer is regulated at around 10,000 to 1,000,000, although depending on the ratio of the macro-monomers and monomer used and the kind of the polar solvent used.

Besides the macro-monomers represented by the above formulas (4) to (6) and styrene, the other monomers may be used as long as the effect of the present invention is not impaired. For example, as the polymer structure, there can be allowed to be incorporated polymethacrylic acid, polymethylmethacrylate, polyvinylpyridine, polyvinylpyrolidone, polyvinylamine, polyacrylic acid, polyethylene glycol, polypropylene glycol, or the like.

Secondly, a fluorescence luminescent material is incorporated into the resulting polymer fine particles. The fluorescence luminescent material similar to that mentioned above may be used. The preferred fluorescence luminescent material is also similar to that described above. The method of incorporating the fluorescence luminescent material into the polymer fine particles is not particularly limited. For example, in the case of the fluoresceinated cholesterol, that is the preferred fluorescence luminescent material mentioned above, the fluorescence luminescent material can be incorporated into the polymer fine particles by impregnating the polymer fine particles into the fluorescence luminescent material in an organic polar solvent such as ethanol.

For example, the polymer fine particles obtained by the above mentioned method are dispersed in ethanol; with the resulting dispersion is mixed an ethanol solution of the fluoresceinated cholesterol; 10 times of ion-exchanged water are added with stirring; the resulting mixture is freeze-dried to obtain polymer fine particles that incorporate the fluoresceinated cholesterol.

Further, when the macro-monomer represented by the above formula (4) and/or the macro-monomer represented by the above formula (5), the macro-monomer represented by the above formula (6), and styrene are polymerized in the polar solvent, the fluorescence luminescent material is allowed to be present in the polymerization system, so that the fluorescence luminescent material can be incorporated into the polymer fine particles at the same time with the formation of the polymer fine particles.

Then, an antibody and/or lectin is bonded or adsorbed on the surfaces of the polymer fine particles that contain the fluorescence luminescent material incorporated therein as described above.

The antibody and lectin used here are the same as described above, and the preferred antibody and lectin are also the same as described above.

The method of bonding or adsorbing the antibody and/or lectin on the surfaces of the polymer fine particles is not particularly limited, but any of covalent bonding and physisorption can be applied, but covalent bonding is preferred.

The method of bonding the antibody and/or lectin on the surface of the polymer fine particles through covalent bonding is also not particularly limited, but the most preferred method is that a condensation agent (for example, carbodiimide or the like) that is generally used to fix proteins or peptides is employed for the incorporation by way of forming an amide bonding. There is not any particular limitation on the condensation agent used here, but 1,3-dicyclohexyl carbodiimide (DCCD) and 1-ethyl-3-(3'-dimethylaminopropyl) carbodiimide (WSCI) are preferred in particular.

EXAMPLES

The present invention will be further described in detail with reference to the following Examples, but it should be construed that the present invention is not limited to those Examples.

[Preparation of Macro-Monomer A]

To 250 mL of toluene were added 50 g of N-vinylacetamide, 18.4 g of 2-mercaptoethanol, and 0.96 g of N,N-azobisisobutylonitrile; the resulting reaction solution was stirred and refluxed at 60° C. for 6 hours with nitrogen gas bubbling; and then, the resulting precipitate was dissolved in ethanol, and was re-precipitated in acetone to obtain 24 g of a reaction product. The reaction product, that is an N-vinylacetamide polymer, was analyzed by size elimination chromatography (SEC) to obtain the molecular weights of Mw/Mn=14,000/5,000. The number corresponding to n in the foregoing formula (4) was about 60.

In 100 mL of DMF, 20 g of the resulting N-vinylacetamide polymer were dissolved; 0.26 g of NaH (oil dispersion) and 0.34 g of tetrabutylphosphonium bromide were added, and then the resulting reaction solution was stirred at room temperature for 3 hours; 2.6 g of 4-vinylbenzylchloride were added, and the reaction solution was further stirred at room temperature for 24 hours; then, the reaction solution was re-precipitated in a mixed solvent of water/methanol=1/1 to obtain 15 g of a reaction product. The reaction product, that is, an end-functionalized N-vinylacetamide polymer with vinylbenzyl, was analyzed by $^1$H-NMR. There was identified a peak assigned to the vinylbenzyl proton. Thus obtained N-vinylacetamide polymer was named as macro-monomer A.

[Preparation of Macro-Monomer B]

In 100 mL of THF were dissolved 50 g of tert-butylmethacrylate, 0.29 g of 2-mercaptoethanol, and 0.55 g of N,N-azobisisobutylonitrile; the resulting reaction solution was stirred and refluxed at 60° C. for 6 hours with nitrogen gas bubbling; and then, the reaction solution was re-precipitated in a mixed solvent of water/methanol=1/1 to obtain 35 g of a reaction product. The reaction product, that is, a tert-butylmethacrylate polymer, was analyzed by size elimination chromatography (SEC) to obtain the molecular weights of Mw/Mn=18,000/9,600. The number corresponding to k in the foregoing formula (6) was about 70.

In 400 mL DMF, 20 g of the resulting tert-butylmethacrylate polymer were dissolved; 0.43 g of NaH (oil dispersion) and 3.20 g of tetrabutylphosphonium bromide were added, and the resulting reaction solution was stirred at room temperature for 3 hours, 3.0 g of 4-vinylbenzylchloride were further added, and the reaction solution was stirred at room temperature for 24 hours; and then, the reaction solution was re-precipitated in a mixed solvent of water/methanol=1/1 to obtain 18 g of a reaction product. Then, 18 g of the resulting reaction product were dissolved in 200 mL of ethanol; 20 mL of concentrated hydrochloric acid and 0.8 g of hydroquinone were added to the ethanol solution, which was then refluxed at 70° C. for 6 hours so as to hydrolyze the reaction product into polymethacrylic acid. After the ethanol was distilled off, the remaining solvent was replaced by ion-exchanged water. The reaction product was further dialyzed with ion-exchanged water until the reaction product showed pH-neutral. And then, the reaction product was freeze-dried to obtain an end-functionalized methacrylic acid polymer with vinylbenzyl. The resulting end-functionalized methacrylic acid polymer with vinylbenzyl was analyzed by $^1$H-NMR. A peak assigned to the vinylbenzyl proton was identified. Thus prepared methacrylic acid polymer was named as macro-monomer B.

[Preparation of Macro-Monomer C]

To 250 mL of ethanol were added 50 g of N-vinylacetamide, 23.0 g of 2-mercaptoethanol, and 0.96 g of N,N-azobisisobutylonitrile; the resulting reaction solution was stirred and refluxed at 60° C. for 6 hours with nitrogen gas bubbling; and then, the resulting reaction solution was admixed with 50 mL of ethanol, and was re-precipitated in acetone to obtain 16.1 g of a reaction product. The reaction product, that is an N-vinylacetamide polymer, was analyzed by size elimination chromatography (SEC) to obtain the molecular weights of Mw/Mn=9,500/4,000. The number corresponding to n in the foregoing formula (4) was about 50.

In 100 mL DMF, 20 g of the resulting N-vinylacetamide polymer were dissolved; 0.26 g of NaH (oil dispersion) and 0.34 g of tetrabutylphosphonium bromide were added, and then the resulting reaction solution was stirred at room temperature for 3 hours; then 2.6 g of 4-vinylbenzylchloride were added, and the reaction solution was further stirred at room temperature for 24 hours; then, the reaction solution was re-precipitated in a mixed solvent of water/methanol=1/1 to obtain 15 g of a reaction product. The reaction product, that is, an end-functionalized N-vinylacetamide polymer with vinylbenzyl, was analyzed by $^1$H-NMR. There was identified a peak assigned to the vinylbenzyl group. Thus obtained N-vinylacetamide polymer was named as macro-monomer C.

[Preparation of Fluoresceinated Cholesterol]

In 5 mL of dehydrated DMF, 200 mg of cholesterol (manufactured by Sigma-Aldrich Corp., Sigma grade) were dissolved; to the resulting solution were added 10 mg of fluorescein-5-carbonylazide, diacetate (F6218, manufactured by Molecular Probes Corp.); after the solution was refluxed at 80° C. for 1 hour, one drop of a 50% hydroxyamine aqueous solution (manufactured by Wako Pure Chemical Industries, Ltd.) was added, and then the solution was further stirred for 30 minutes; then, ion-exchanged water was added to the solution so as to precipitate a reaction product. In this way, a fluoresceinated cholesterol was obtained. The incorporation of fluorescein group was identified by fluorescence luminescence measurement and high performance liquid chromatography (HPLC). Further, the fluoresceinated cholesterol was confirmed not to dissolve in ion-exchanged water and physiological saline solution by UV-vis spectrometer (V-550, manufactured by JEOL Ltd.). The fluorescein concentration in the fluoresceinated cholesterol was 1% by mass.

Example 1

In a mixed solution of 5 mL of ion-exchanged water and 10 mL of ethanol, 1.0 g of the macro-monomer A obtained as described above, 1.0 g of styrene, and 15 mg of N,N-azobisisobutylonitrile were dissolved; after 30 minutes of nitrogen gas bubbling, the resulting solution was sealed and shaken in a 60° C. water bath for 24 hours to form fine particles.

The fine particles were centrifugally separated and freeze-dried to obtain objective fine particles. The fine particles had an average diameter of 400 nm (as measured with the dynamic light scattering method).

To 100 mg of the fine particles thus obtained, 5 mg of the fluoresceinated cholesterol obtained as described above were added. After the resulting mixture was dispersed in 5 mL of ethanol, 10 times in volume of ion-exchanged water were further added with stirring. Then, the fine particles were centrifugally separated and dispersed again in ion-exchanged water. This separation and dispersing process was repeated three times. Then, the fine particles were freeze-dried to obtain fine particles that incorporated the fluoresceinated cholesterol as an identification material (labeled fine particles).

The labeled fine particles thus obtained in an mount of 10 mg were added and dispersed by stirring in a solution that dissolves 1 mg of peanut lectin in 1 mL of a phosphate buffered saline solution (trade name: Dulbecco's Phosphate Buffered Saline D8537, manufactured by Sigma-Aldrich Corp., hereinafter, abbreviated as PBS). The resulting dispersion was shaken at 4° C. for 24 hours so as to adsorb the peanut lectin on the surfaces of the labeled fine particles. After that, the process of centrifugal separation and re-dispersion in PBS was repeated three times to remove the peanut lectin that was not adsorbed. Finally, in a state of being dispersed in a phosphate buffered saline solution (containing Ca and Mg) (trade name: Dulbecco's Phosphate Buffered Saline D8662, manufactured by Sigma-Aldrich Corp., hereinafter, abbreviated as PBS(Ca+Mg)), a diagnostic marker 1 of the present invention was obtained.

Example 2

In a mixed solution of 5 mL of ion-exchanged water and 10 mL of ethanol, 0.75 g of the macro-monomer A obtained as described above, 0.25 g of the macro-monomer B obtained as described above, 1.0 g of styrene, and 15 mg of N,N-azobisisobutylonitrile were dissolved; after 30 minutes of nitrogen gas bubbling, the resulting solution was sealed and shaken in a 60° C. water bath for 24 hours to form fine particles. The fine particles were centrifugally separated and freeze-dried to obtain objective fine particles. The fine particles had an average diameter of 470 nm (as measured with the dynamic light scattering method).

To 100 mg of the fine particles thus obtained, similarly to Example 1, the fluoresceinated cholesterol was incorporated as an identification material and to obtain labeled fine particles.

In 800 μL of a 0.05M-$KH_2PO_4$ aqueous solution were dispersed 10 mg of the labeled fine particles obtained above. To the resulting dispersion were added 200 μL of a 0.05 M-$KH_2PO_4$ aqueous solution that was prepared in advance by dissolving 1% by mass of a water-soluble carbodiimide [1-ethyl-3-(3'-dimethylaminopropyl) carbodiimide]. After the resulting mixture was shaken at 4° C. for 30 minutes, the mixture was subjected to centrifugal separation (6,000 rpm, 10 minutes) and the resulting supernatant was removed from the mixture. Then, to the mixture was added a solution that dissolved 1 mg of peanut lectin in 1 mL PBS, and was stirred to disperse the labeled fine particles. The dispersion thus prepared was shaken at 4° C. for 24 hours to bond the peanut lectin on the surfaces of the labeled fine particles. Then, the process of centrifugal separation and re-dispersion in PBS was repeated three times to remove unreacted peanut lectin. Finally, in a state of being dispersed in PBS(Ca+Mg), a diagnostic marker 2 of the present invention was obtained.

Example 3

In a mixed solution of 5 mL of ion-exchanged water and 10 mL of ethanol, 0.50 g of the macro-monomer A obtained as described above, 0.50 g of the macro-monomer B obtained as described above, 1.0 g of styrene, and 15 mg of N,N-azobisisobutylonitrile were dissolved; after 30 minutes of nitrogen gas bubbling, the resulting solution was sealed and shaken in a 60° C. water bath for 24 hours to form fine particles. The fine particles were centrifugally separated and freeze-dried to obtain objective fine particles. The fine particles had an average diameter of 400 nm (as measured with the dynamic light scattering method).

With respect to 100 mg of the fine particles thus obtained, similarly to Example 2, the fluoresceinated cholesterol was incorporated as an identification material to obtain labeled fine particles.

To 10 mg of the resulting labeled fine particles, similarly to Example 2, peanut lectin was bonded on the surfaces of the labeled fine particles. In this way, a diagnostic marker 3 of the present invention in a state of being dispersed in PBS(Ca+Mg) was obtained.

Example 4

Except that the amount of the macro-monomer A was changed to 0.25 g and the amount of the macro-monomer B was changed to 0.75 g, fine particles were obtained similarly to Example 3. The fine particles had an average diameter of 360 nm (as measured with the dynamic light scattering method).

The resulting fine particles were labeled in a similar manner to Example 3. Then, also similarly to Example 3, peanut lectin was bonded on the surfaces of the labeled fine particles.

In this way, a diagnostic marker 4 of the present invention in a state of being dispersed in PBS(Ca+Mg) was obtained.

Example 5

Except that the amount of peanut lectin used was changed to 0.125 mg when the peanut lectin was bonded on the surfaces of the labeled fine particles that were obtained in Example 4, the peanut lectin was bonded on the surfaces of the labeled fine particles in a similar manner to Example 4. In this way, a diagnostic marker 5 of the present invention in a state of being dispersed in PBS(Ca+Mg) was obtained.

Example 6

In a mixed solution of 5 mL of ion-exchanged water and 10 mL of ethanol, 0.5 g of the macro-monomer B obtained as described above, 0.5 g of the macro-monomer C obtained as described above, 1.0 g of styrene, and 15 mg of N,N-azobisisobutylonitrile were dissolved; after 30 minutes of nitrogen gas bubbling, the resulting solution was sealed and shaken in a 60° C. water bath for 24 hours to form fine particles.

The fine particles were centrifugally separated and freeze-dried to obtain objective fine particles. The fine particles had an average diameter of 230 nm (as measured with the dynamic light scattering method).

To 100 mg of the fine particles thus obtained, similarly to Example 2, the fluoresceinated cholesterol was incorporated as an identification material to obtain labeled fine particles.

To 10 mg of the resulting labeled fine particles, similarly to Example 2, peanut lectin was bonded on the surfaces of the labeled fine particles. In this way, a diagnostic marker 6 of the present invention in a state of being dispersed in PBS(Ca+Mg) was obtained.

Example 7

In a mixed solution of 5 mL of ion-exchanged water and 10 mL of ethanol, 0.5 g of the macro-monomer B obtained as described above, 0.5 g of the macro-monomer C obtained as described above, 1.0 g of styrene, 15 mg of N,N-azobisisobutylonitrile, and further 2 mg of coumarin6 (Coumarin 6, manufactured by Sigma-Aldrich Corp.) were dissolved; after 30 minute nitrogen gas bubbling, the resulting solution was sealed and shaken in a 60° C. water bath for 24 hours to form labeled fine particles that contained coumarin 6 incorporated therein.

These labeled fine particles were centrifugally separated and freeze-dried to obtain objective labeled fine particles. The labeled fine particles had an average diameter of 230 nm (as measured with the dynamic light scattering method).

Peanut lectin was bonded to the surfaces of the labeled fine particles in a similar manner to Example 2. In this way, a diagnostic marker 7 of the present invention in a state of being dispersed in PBS(Ca+Mg) was obtained.

Comparative Example 1

A solution that dissolves 1.0 mg of fluoresceinated peanut lectin (peanut agglutinin, Fluorescein, manufactured by Funakoshi Corp.) in 1 mL PBS(Ca+Mg) was used as a comparative diagnostic marker 1.

Comparative Example 2

In a mixed solution of 5 mL of ion-exchanged water and 10 mL of ethanol, 1.0 g of the macro-monomer B obtained as described above, 0.75 g of styrene, and 15 mg of N,N-azobisisobutylonitrile were dissolved; after 30 minutes of nitrogen gas bubbling, the resulting solution was sealed and shaken in a 60° C. water bath for 24 hours to form fine particles.

The fine particles were centrifugally separated and freeze-dried to obtain objective fine particles. The fine particles had an average diameter of 300 nm (as measured with the dynamic light scattering method).

The fine particles thus obtained were labeled in a similar manner to Example 2. Similarly to Example 5, peanut lectin was bonded to the surfaces of the labeled fine particles. In this way, a comparative diagnostic marker 2 in a state of being dispersed in PBS(Ca+Mg) was obtained.

Comparative Example 3

The labeled fine particles (the fine particles before the peanut lectin was bonded) that are prepared in Example 3 were dispersed in PBS(Ca+Mg) and were used as a comparative diagnostic marker 3.

[Evaluation Tests]

For the diagnostic markers 1 to 7 prepared in Examples 1 to 7 and the comparative diagnostic markers 1 to 3 prepared in Comparative Examples 1 to 3, the following evaluation tests were carried out. The results are shown in Table 1.

[Analysis of Surface Composition of Fine Particles]

The surface composition of the fine particles was analyzed by X-ray photoelectron spectroscopy (with a spectrometer of AXIS-ULTA manufactured by KRATOS ANALYTICAL Corp., using a charge compensation electron gun and a monochromatic Al-Xray source). The depth for analysis was set at about 10 nm. The results obtained by the present analysis reflected the elemental composition of the fine particle surface in the present invention.

Based on the amount (in % by mass) of nitrogen atom that was obtained from the integrated value of areas under each peak of C1s, O1s, and N1s, the amount (in % by mass) of —$CH_2$—CH(—NH—CO—$CH_3$)— group was estimated.

[Peanut Lectin Bonded Amount]

The amount of peanut lectin bonded (or adsorbed) per 1 g of each diagnostic marker and each comparative diagnostic marker was determined in accordance with the ninhydrin method.

[Evaluation Test for Specific Bonding Ability to TF Antigen]

Thomsen-Friedenreich (TF) antigen that are expressed on the mucosal surface of large intestine cancer possesses on its surface β-galactocyl-(1,3)-α-N-acetylgalactosamine residue in high density. Red blood cells treated with sialidase were used as a model of the above mucosal surface.

The red blood cells treated with sialidase also possess on their surfaces the β-galactocyl-(1,3)-α-N-acetylgalactosamine residue in high density. The specific bonding ability of each diagnostic marker and each comparative diagnostic marker to these red blood cells was evaluated, as specifically described below.

Three mL of stored rabbit blood were diluted by 5 times with PBS. The blood was centrifugally separated at 2,000 rpm for 5 minutes, and after the supernatant was discarded, the blood was diluted again by 5 times with PBS. This operation was repeated three times to yield a red blood cell fraction.

The red blood cell fraction was added to the equivalent quantity of 1 U/mL sialidase (derived from *Arthrobactor ureafaciens*, manufactured by F. Hoffmann-La Roche Ltd), and shaken gently at 37° C. for 1 hour. The resulting mixture was diluted by 4 times with PBS, centrifugally separated at 2,000 rpm for 5 minutes, and then dispersed in PBS(Ca+Mg). The resulting dispersion was centrifugally separated at 2,000 rpm for 5 minutes, and dispersed again in PBS(Ca+Mg). This operation was repeated three times to yield a red blood cell fraction treated with sialidase.

A PBS(Ca+Mg) solution (or red blood cell suspension) suspending 2% v/v of the red blood cells treated with sialidase was prepared from the red blood cell fraction thus obtained. In each well in the second and later tiers of a 96-Well Multi-Tier Microtiter plate (with U-bottom), PBS(Ca+Mg) was dispensed in an amount of 50 μL each. Each sample solution (each diagnostic marker and each comparative diagnostic marker), that was prepared in a manner that the concentration of the peanut lectin became equal for every sample solution on the basis of the amount of lectin bonded, was dispensed in an amount of 100 μL in each well of the first tier. In this way, a tier with 2 fold dilution was prepared.

The red blood cell suspension treated with sialidase was dispensed in an amount of 50 μL in each well, and left standing at room temperature for 60 minutes. The bonding ability was evaluated by the precipitation condition (presence or absence of aggregation) on the bottom of the well. The precipitate that aggregated as a clump on the bottom was firmly aggregated, and was evaluated to have a low bonding ability to the diagnostic marker (negative). The precipitate that spread and deposited at the bottom was evaluated to have a high bonding ability to the diagnostic marker (positive). The lowest concentration after mixing the red blood cell suspension showing positive was regarded as the lowest bonding ability concentration (peanut lectin concentration). In the present evaluation, the specific bonding ability to the TF antigen can be evaluated to be higher as the lowest bonding active concentration is lower.

[Evaluation Test for Bonding Ability to Digestive Organ Mucosa]

Considering that the normal mucosa or cell possesses on its surface various forms of sugar chains, an aggregation-active evaluation test similar to the above evaluation test was performed using red blood cells that also have on their surfaces a various forms of sugar chains. The bonding ability to digestive organ mucosa was evaluated for each diagnostic marker and each comparative diagnostic marker, specifically as described below.

Three mL of stored rabbit blood were diluted by 5 times with PBS. The blood was centrifugally separated at 2,000 rpm for 5 minutes, and after the supernatant was discarded, the blood was diluted again by 5 times with PBS. This operation was repeated three times to yield a red blood cell fraction. A PBS(Ca+Mg) suspending 2% v/v of the red blood cells was prepared from the red blood cell fraction thus obtained. In each well in the second and later tiers of a 96-Well Multi-Tier Microtiter plate (with U-bottom), PBS(Ca+Mg) was dispensed in an amount of 50 μL each. Each sample solution (each diagnostic marker and each comparative diagnostic marker), that was prepared in a manner that the concentration of the peanut lectin became equal for every sample solution on the basis of the amount of lectin bonded, was dispensed in an amount of 100 μL in each well of the first tier. In this way, a tier with 2 fold dilution was prepared.

The red blood cell suspension was dispensed in an amount of 50 μL in each well, and left standing at room temperature for 60 minutes. The bonding ability was evaluated by the precipitation condition (presence or absence of aggregation) on the bottom of the well. The precipitate that aggregated as a clump on the bottom was firmly aggregated, and was evaluated to have a low bonding ability to the diagnostic marker (negative). The precipitate that spread and deposited at the bottom was evaluated to have a high bonding ability to the diagnostic marker (positive). The lowest concentration after mixing the red blood cell suspension showing positive was regarded as the lowest bonding ability concentration (peanut lectin concentration). In the present evaluation, the bonding ability to the digestive organ mucosa can be evaluated to be lower as the lowest bonding active concentration is higher.

[Identification Capability Evaluation by Fluorescence Microscope]

The red blood cell suspension treated with sialidase and the red blood cell suspension, each used for the above evaluation tests for the specific bonding ability to the TF antigen and the bonding ability to digestive organ mucosa, were mixed in a ratio of 1:1 (by volume) to prepare a sample. The sample was cast on a nonluminescent glass slide, and was observed with a confocal laser scanning microscope (LSM5 Pascal, manufactured by Carl Zeiss Corp.) using an exciting light with a wavelength of 475 nm. The evaluation criteria are as follows.

[Contrast]

Good: fluorescent blood cell and non-fluorescent blood cell can be easily differentiated; and Poor: fluorescent blood cell and non-fluorescent blood cell cannot be differentiated, or are not easy to differentiate.

Fluorescence Intensity

Good: fluorescence luminescent portions can be clearly identified in the form of particulates; and Poor: fluorescence luminescence is broadly dispersed, and light is emitted from the whole body of the blood cell.

TABLE 1

|  | Examples | | | | | | | Comparative Examples | | |
| --- | --- | --- | --- | --- | --- | --- | --- | --- | --- | --- |
|  | 1 | 2 | 3 | 4 | 5 | 6 | 7 | 1 | 2 | 3 |
| Macro-monomer mass ratio (A/B/C) | 100/0/0 | 75/25/0 | 50/50/0 | 25/75/0 | 50/50/0 | 0/50/50 | 0/50/50 | — | 0/100/0 | 50/50/0 |
| —$CH_2$—CH(—NH—CO—$CH_3$)— group content (% by mass) | 49 | 55 | 41 | 50 | 41 | 46 | 46 | — | 0 | 41 |
| Peanut lectin bonded amount (mg/g) | 5.7 | 3.8 | 3.8 | 5.7 | 1.2 | 5.2 | 5.2 | — | 7.0 | 0 |
| Lowest bonding ability concentration in evaluation of specific bonding ability to TF antigen (μg/mL) | 62.5 | 7.8 | 7.8 | 15.6 | 31.3 | 1.0 | 1.0 | 0.13 | 1.0 | (*) |

TABLE 1-continued

| | | Examples | | | | | | | Comparative Examples | | |
|---|---|---|---|---|---|---|---|---|---|---|---|
| | | 1 | 2 | 3 | 4 | 5 | 6 | 7 | 1 | 2 | 3 |
| Lowest bonding ability concentration in evaluation of bonding ability to digestive organ mucosa (μg/mL) | | 125 or more | 125 or more | 125 or more | 62.5 | 125 or more | 125 or more | 125 or more | 7.8 | 1.0 | (*) |
| Fluorescence identification capability | Contrast | Good | Good | Good | Good | Good | Good | Good | Good | Poor | Poor |
| | Fluorescence | Good | Good | Good | Good | Good | Good | Good | Poor | Good | Good |

(*): No peanut lectin was used in these cases, so that the evaluation test was performed conveniently in a similar initial concentration to Example 3 where the same labeled fine particles were used. The results were 125 or more for both cases.

INDUSTRIAL APPLICABILITY

The effect of the present invention is that a diagnostic marker capable of enhancing the contrast between the cancer tissues and normal tissues and advantageous for early detection and treatment of digestive cancers using an endoscope, and a method for producing the diagnostic marker were provided.

The invention claimed is:

1. A diagnostic marker comprising particles having a diameter of from 1 nm to 100 μm,
    the particles possessing on their surfaces:
    a site comprising lectin having a high specific bonding ability to a specific antigen residing on the mucosa of digestive cancers, said lectin bonded on the surface of the particles by covalent bonding; and
    a site comprising at least one of a structure represented by formula (1) and a structure represented by formula (2) having a low bonding ability to the mucosa of digestive organs,

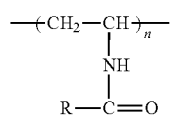
(1)

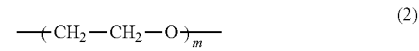
(2)

wherein, m is any number of from 10 to 400, and the particles incorporating an identification material for detecting the particle, said material being incorporated in the course of particle synthesis so as to be sandwiched between the molecules of the particle, or incorporated by absorption into the inside of the particles after the particles are synthesized.

2. The diagnostic marker according to claim 1, wherein the identification material is a fluorescence luminescent material.

3. The diagnostic marker according to claim 1, wherein the site having a high specific bonding ability to a specific antigen residing on the mucosa of digestive cancers is antibody and lectin.

4. The diagnostic marker according to claim 1, wherein the particles contain as a principal ingredient a polymer having a structure that is represented by formula (3),

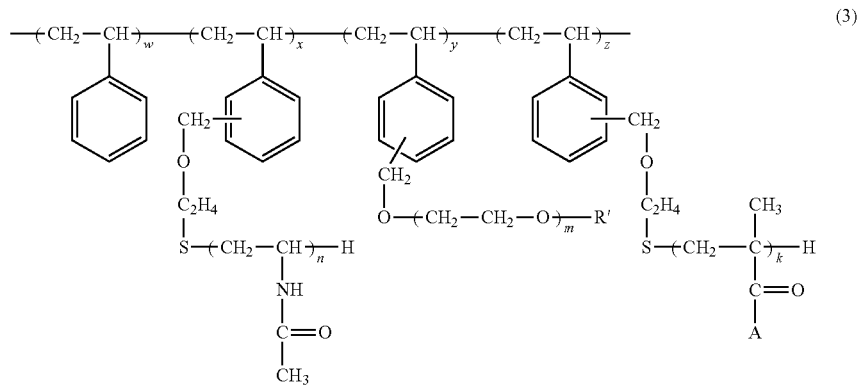
(3)

wherein, R is hydrogen atom or a hydrocarbon group having from 1 to 4 carbon atoms; and n is any number of from 10 to 400, wherein, R' is hydrogen atom or a hydrocarbon group having from 1 to 4 carbon atoms; n is the same as in the formula (1); m is the same as in the formula (2); k is any number of from 10 to 200; A is lectin; w, x, y, and z, each is a number that allows the present polymer to have a molecular weight of from 10,000 to 1,000,000, and (x+y):z:w is from 1:0.2 to 2.5:5 to 300; either one of x and y may be 0; and the order of each repeating unit corresponding to each repeating number of w, x, y, and z is arbitrary in the main chain of the present polymer.

5. The diagnostic marker according to claim 1, wherein the particles are inorganic particles or organic polymers.

6. The diagnostic marker according to claim 5, wherein the organic polymers are polystyrene or poly(meth)acrylate.

* * * * *